United States Patent
Alshemari

(10) Patent No.: US 8,480,611 B1
(45) Date of Patent: Jul. 9, 2013

(54) MIDDLE EAR VENTILATION TUBE

(71) Applicant: Hasan M. Sh. Sh. Alshemari, Saad Al Abdulla (KW)

(72) Inventor: Hasan M. Sh. Sh. Alshemari, Saad Al Abdulla (KW)

( * ) Notice: Subject to any disclaimer, the term of this patent is extended or adjusted under 35 U.S.C. 154(b) by 0 days.

(21) Appl. No.: 13/633,777

(22) Filed: Oct. 2, 2012

(51) Int. Cl.
*A61M 5/00* (2006.01)

(52) U.S. Cl.
USPC ............................................. 604/8; 604/174

(58) Field of Classification Search
USPC .............................................................. 604/8
See application file for complete search history.

(56) References Cited

U.S. PATENT DOCUMENTS

| | | | |
|---|---|---|---|
| 1,497,722 A | | 6/1924 | Holst-Grubbe |
| 3,948,271 A | | 4/1976 | Akiyama |
| 4,015,607 A | * | 4/1977 | Wright, III ................. 623/23.64 |
| 4,094,303 A | | 6/1978 | Johnston |
| 4,326,512 A | * | 4/1982 | Peerless ....................... 128/868 |
| D274,753 S | * | 7/1984 | Armstrong ..................... D24/34 |
| 4,744,792 A | | 5/1988 | Sander et al. |
| 5,246,455 A | | 9/1993 | Shikani |
| 5,645,584 A | | 7/1997 | Suyama |
| 5,746,725 A | | 5/1998 | Shalon et al. |
| 6,358,222 B1 | | 3/2002 | Grundei |
| 6,692,455 B2 | | 2/2004 | Goode et al. |
| 2003/0018291 A1 | * | 1/2003 | Hill et al. ........................... 604/8 |
| 2009/0099573 A1 | * | 4/2009 | Gonzales ....................... 606/108 |

FOREIGN PATENT DOCUMENTS

WO  WO 2005/082303  * 9/2005

* cited by examiner

*Primary Examiner* — Leslie Deak
*Assistant Examiner* — Jordan B Bailey
(74) *Attorney, Agent, or Firm* — Richard C. Litman

(57) ABSTRACT

The middle ear ventilation tube is a drainage tube for placement through an opening formed through the tympanic membrane to drain fluid from the middle ear to the ear canal or outer ear. The middle ear ventilation tube includes a hollow, substantially cylindrical tube having axially opposed first and second open ends and a pair of diametrically opposed lateral drainage openings adjacent the first open end, thereby providing the tube with three drainage openings (the axial open first end and the two lateral openings). An annular flange is formed about the second open end and extends outwardly therefrom. In use, the tube is inserted through an opening formed through the tympanic membrane of a patient's ear so that the annular flange is positioned against the tympanic membrane within the middle ear, and the first open end and the pair of diametrically-opposed openings are positioned within the patient's ear canal.

4 Claims, 5 Drawing Sheets

MIDDLE EAR VENTILATION TUBE

BACKGROUND OF THE INVENTION

1. Field of the Invention

The present invention relates to drainage and ventilation tubes for the middle ear, and particularly to a middle ear ventilation tube having auxiliary openings for preventing clogging of the tube.

2. Description of the Related Art

The installation of tubes in the tympanic membrane, which separates the middle ear from the outer ear, is a well-known remedy for treating inflammation of the middle ear, or otitis media. Typically, a myringotomy is performed to create an opening in the tympanic membrane, and a vent or drain in the form of a tube is inserted into the opening to permit drainage of fluid from the middle ear to alleviate a buildup or reduction of pressure in the middle ear cavity. The tube functions to maintain the opening in the tympanic membrane for a sufficient period of time following the surgery to allow pressure to equalize between the middle and outer ears. Frequently, the condition of buildup or reduction of pressure in the middle ear cavity, which the tube is intended to alleviate, requires that the tube remain in place for a significant period of time, ranging in duration from about six to about twenty-four months.

A variety of ventilation tubes for insertion into an opening in the tympanic membrane have been used over the years. Typical conventional ventilation tubes are generally cylindrical, which allows the tubes to be easily inserted into the myringotomy opening, but are susceptible to accidental extraction from the tympanic membrane. On the other hand, ventilation tubes having anchoring structures are also known and are less likely to be accidentally extracted from the tympanic membrane, but are difficult to insert into, and extract from, the myringotomy openings, tending to enlarge the myringotomy openings such that the tendency of the tubes to fall out of the membrane increases. Thus, although some anchoring is necessary, minimizing the size of the structure is desirable.

Further, typical ventilation tubes suffer from clogging, particularly with extended use. The clogging is often caused by epithelial migration, occlusion by middle ear effusions, or simple buildup of cerumen (i.e., ear wax). The problem of displacement, as described above, can also cause one end of the tube to become at least partially covered and closed off.

The prevention of such clogging and dislodgment of the tube is necessary, since subsequent infection within the ear will cause a pressure build-up of pus and wax behind the tympanic membrane if the middle ear cannot be drained, which, along with dislodging the tube, presents the risk of possibly tearing the membrane as the tube is pushed against or through the tympanic membrane.

Thus, a middle ear ventilation tube solving the aforementioned problems is desired.

SUMMARY OF THE INVENTION

The middle ear ventilation tube is a ventilation tube for placement through an opening formed through the tympanic membrane to drain fluid from the middle ear to the ear canal or outer ear. The middle ear ventilation tube includes a hollow, substantially cylindrical tube having axially opposed first and second open ends. The tube also has a pair of diametrically opposed openings formed adjacent the first open end thereof. An annular flange is formed about the second open end and extends outwardly therefrom.

In use, the hollow, substantially cylindrical tube is inserted through an opening formed through the tympanic membrane of a patient's ear such that the annular flange is positioned against the side of the tympanic membrane within the patient's middle ear, and the first open end and the pair of diametrically-opposed openings are positioned on the opposite side of the tympanic membrane within the patient's ear canal. The diametrically opposed openings are provided to prevent clogging of the cylindrical tube.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
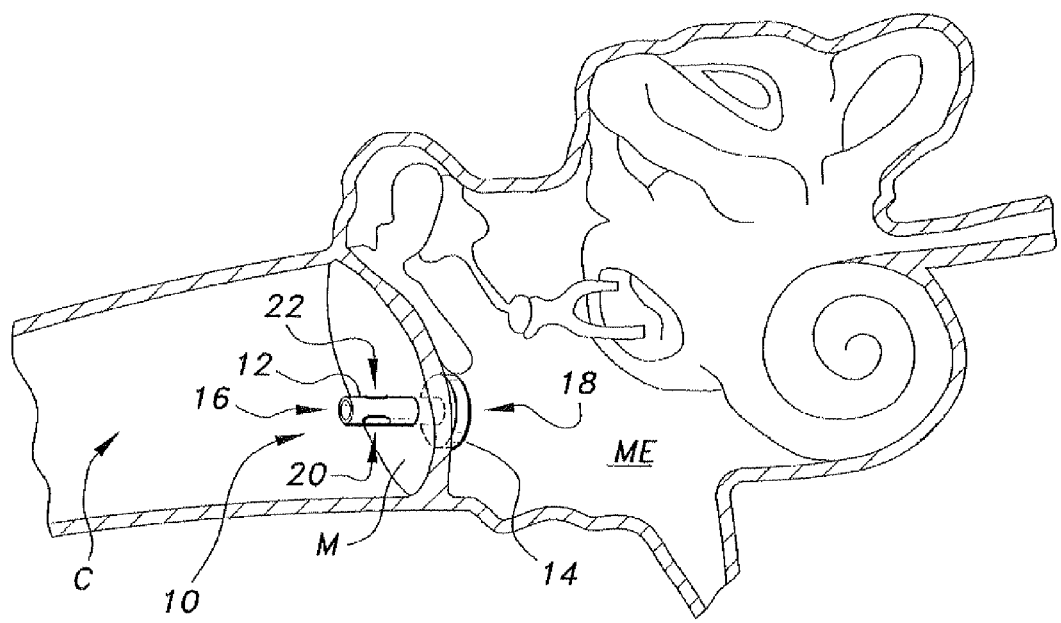
FIG. 1 is an environmental, perspective view of a middle ear ventilation tube according to the present invention.
Figure 2:
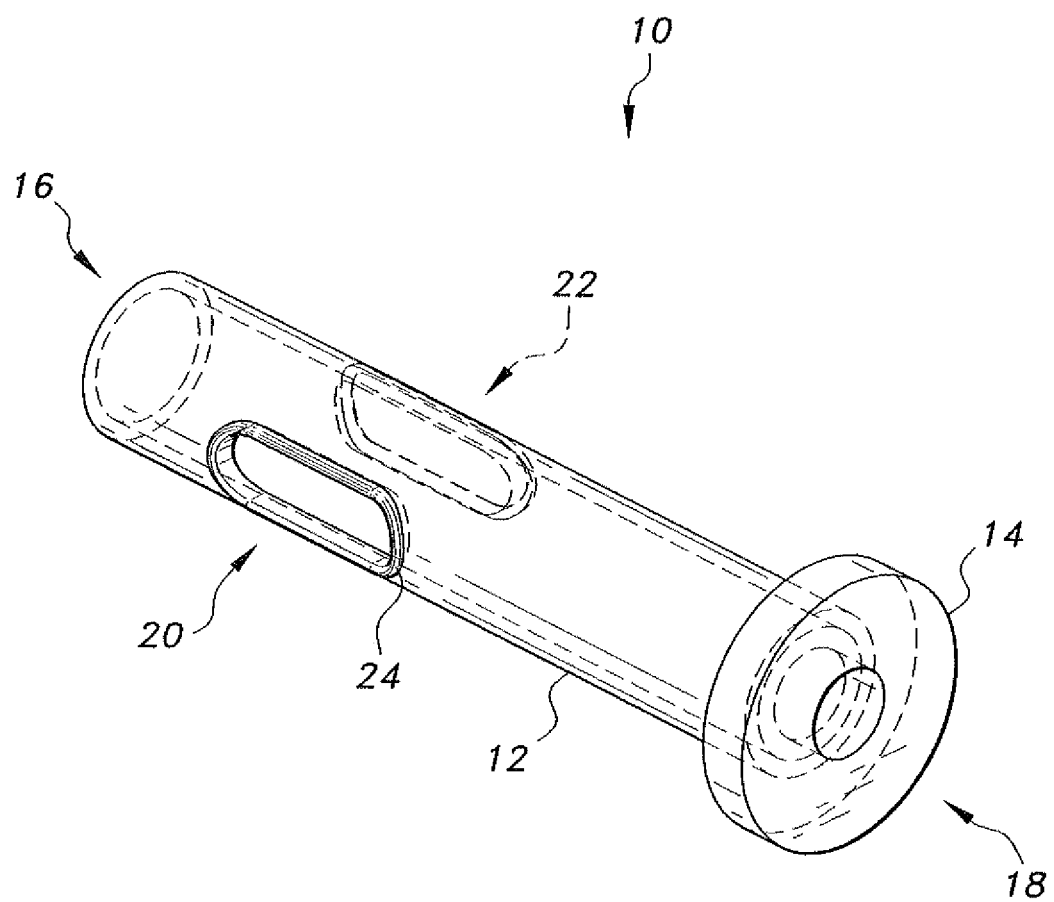
FIG. 2 is a perspective view of the middle ear ventilation tube according to the present invention.
Figure 3:
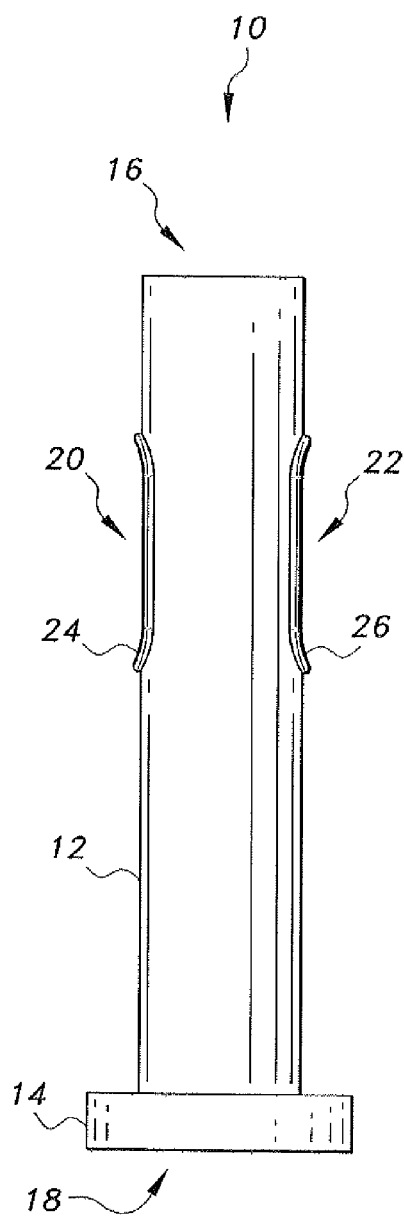
FIG. 3 is a side view of the middle ear ventilation tube of FIG. 2.
Figure 4:
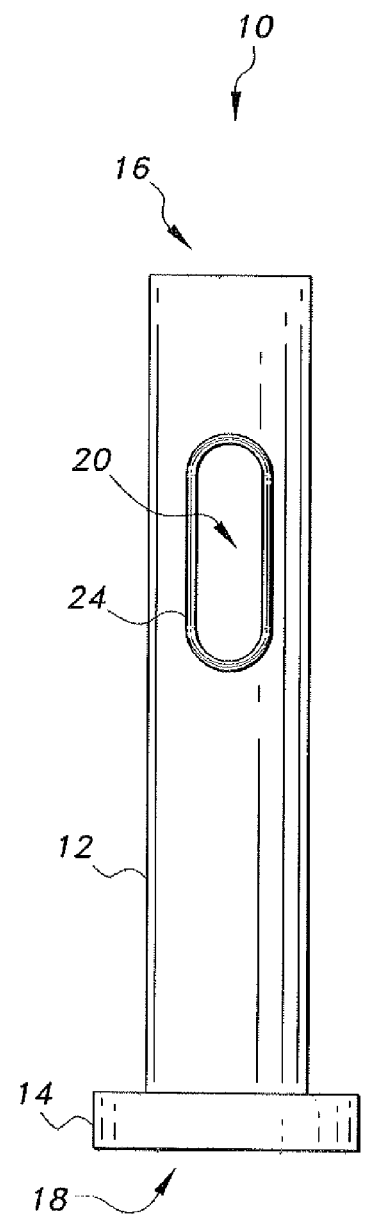
FIG. 4 is a another side view of the middle ear ventilation tube of FIG. 2, shown rotated 90° from the view of FIG. 3.
Figure 5:
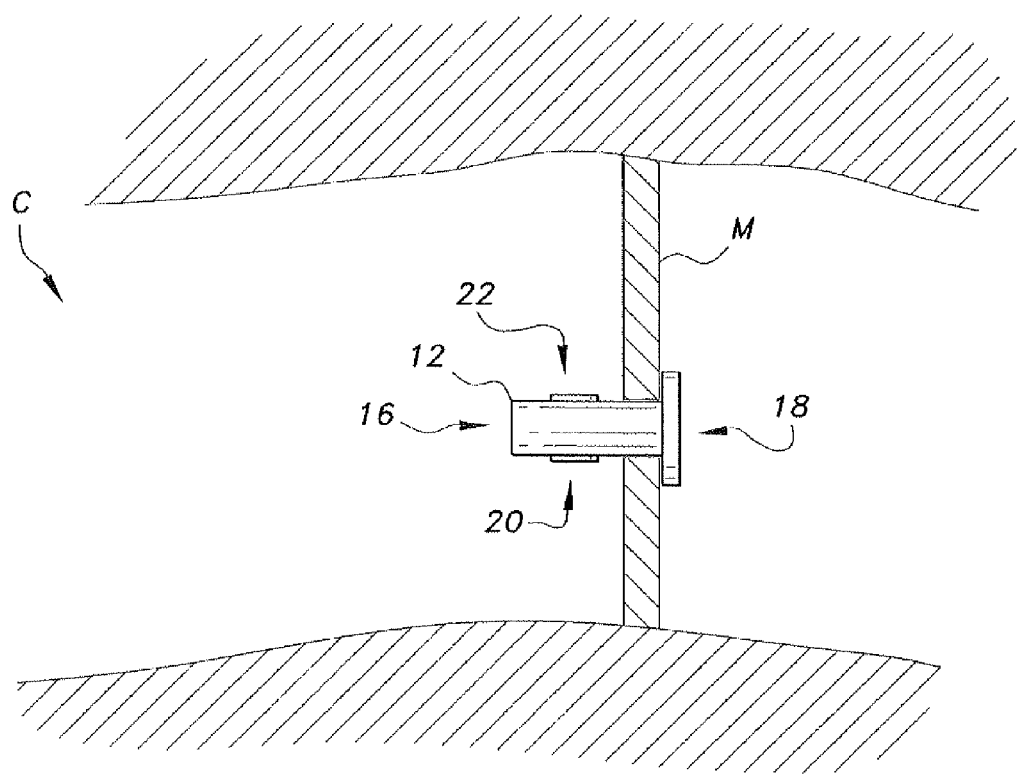
FIG. 5 is an environmental, side view of the middle ear ventilation tube of FIG. 2, showing the tube lodged in the tympanic membrane.

The middle ear ventilation tube 10 is a ventilation tube for placement through an opening formed through the tympanic membrane M to drain fluid from the middle ear ME to the ear canal C or outer ear, as illustrated in FIGS. 1 and 5. The middle ear ventilation tube 10 includes a hollow substantially cylindrical tube 12 having axially opposed first and second open ends 16, 18, respectively. As shown in FIGS. 2, 3 and 4, an annular flange 14 is formed about the second open end 18. The tube 12 also has a pair of diametrically opposed lateral drainage slots or openings 20, 22 formed through the tube 12 adjacent the first open end 16, thereby providing the tube with three drainage openings (the axial open end 16 of the tube 12 and the two lateral openings 20, 22). As best seen in FIG. 5, the annular flange 14, in use, is positioned against one side of the tympanic membrane M within the middle ear ME, thus preventing the middle ear ventilation tube 10 from dislodging when in use. The pair of diametrically opposed openings 20, 22 are positioned within the ear canal C and are provided to bleed off excess fluid to prevent clogging within the tube 12 when fluid drains from the middle ear ME, through the tube 12, and out into the ear canal C through the first open end 16. Preferably, a raised rim 24, 26 is respectively formed about each of the openings 20, 22, as shown, acting further to prevent the middle ear ventilation tube 10 from dislodging. The raised rims 24, 26, and their respective openings 20, 22, are preferably identical in dimension and configuration.

Figure 6:
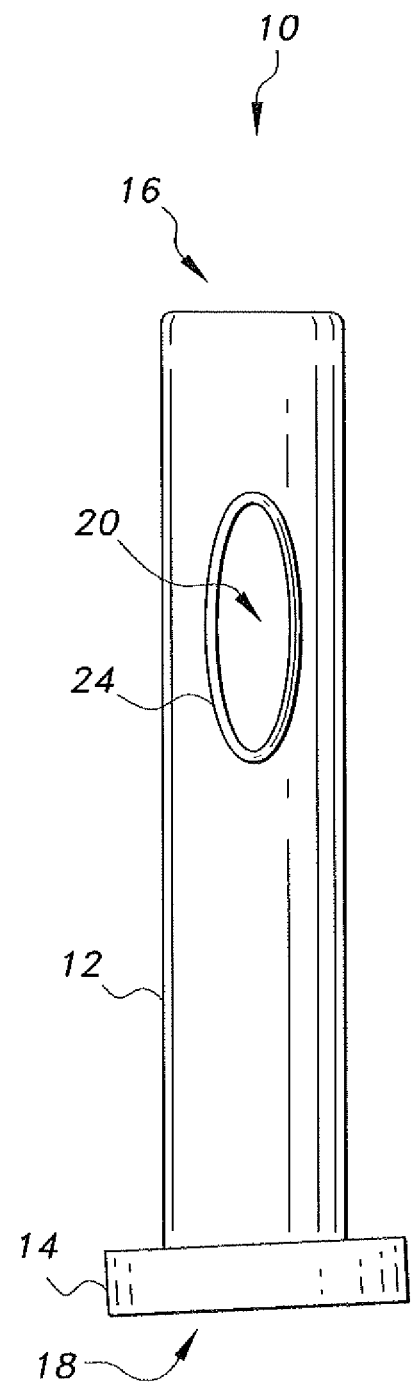
FIG. 6 is a side view of an alternative embodiment of a middle ear ventilation tube according to the present invention.

Although the lateral drainage openings 20, 22, and their respective raised rims 24, 26, are shown as being substantially oval or elliptical, it should be understood that any suitable dimensions or configuration may be utilized. Similarly, although the flange 14 is shown as having an annular shape, it should be understood that the flange 14 may have any desired dimensions or configuration. The middle ear ventilation tube 10 may be formed from any suitable material that is biologically inert and compatible with human tissue. As with conventional ventilation tubes, the length of tube 12 may be varied, but is preferably substantially greater in length than the thickness of tympanic membrane M. Further, although the annular flange 14 is shown as extending along a radial direction orthogonal to the axis of tube 12, it should be understood that the annular flange 14 may be angled with respect to the radial direction, as shown in FIG. 6. Preferably, the angling away from the radial direction is relatively small.

It is to be understood that the present invention is not limited to the embodiments described above, but encompasses any and all embodiments within the scope of the following claims.

I claim:

1. A middle ear ventilation tube, consisting of:
 a hollow, substantially cylindrical tube having axially opposed first and second open ends and a pair of diametrically opposed lateral drainage openings being in the tube adjacent the first open end thereof, wherein each of the lateral drainage openings includes a raised rim about the opening and coextensive therewith; and
 an annular flange formed about the second open end and extending outwardly therefrom, the annular flange defining the terminal portion of the second end and being adapted for insertion through an opening in a patient's tympanic membrane, the flange lodging against the tympanic membrane in the middle ear while the first end of the tube extends through the membrane into the outer ear to drain fluids from the middle ear to the outer ear.

2. The middle ear ventilation tube as recited in claim 1, wherein the annular flange extends outwardly along a radial direction orthogonal to the tube.

3. The middle ear ventilation tube as recited in claim 1, wherein the annular flange extends outwardly at a slight oblique angle from the tube.

4. A middle ear ventilation tube, comprising:
 a hollow tube having axially opposed first and second open ends and a pair of opposed lateral drainage openings being in the tube adjacent the first open end thereof, wherein each of the lateral drainage openings includes a raised rim about the opening and coextensive therewith; and
 an annular flange formed about the second open end and extending outwardly therefrom, the annular flange defining the terminal portion of the second end and being adapted for insertion through an opening in a patient's tympanic membrane, the flange lodging against the tympanic membrane in the middle ear while the first end of the tube extends through the membrane into the outer ear to drain fluids from the middle ear to the outer ear.

* * * * *